(12) United States Patent
McBride

(10) Patent No.: US 8,349,358 B1
(45) Date of Patent: Jan. 8, 2013

(54) TRANSDERMAL ANESTHETIC APPLICATOR HAVING THERMOCHROMIC INDICATION

(76) Inventor: Emily Vann McBride, Santa Ana, CA (US)

( * ) Notice: Subject to any disclaimer, the term of this patent is extended or adjusted under 35 U.S.C. 154(b) by 228 days.

(21) Appl. No.: 12/760,876

(22) Filed: Apr. 15, 2010

(51) Int. Cl.
*A61F 13/00* (2006.01)

(52) U.S. Cl. ........................................ 424/449

(58) Field of Classification Search .................. None
See application file for complete search history.

(56) References Cited

U.S. PATENT DOCUMENTS

| | | | | |
|---|---|---|---|---|
| 5,667,798 | A * | 9/1997 | Royds et al. | 424/449 |
| D454,956 | S * | 3/2002 | Visintainer | D24/189 |
| 6,455,752 | B1 * | 9/2002 | Vesey | 602/41 |
| 2003/0191423 | A1 * | 10/2003 | Sun | 602/58 |
| 2004/0082897 | A1 * | 4/2004 | Rangel et al. | 602/59 |
| 2007/0232979 | A1 * | 10/2007 | Montgomery | 602/58 |
| 2010/0016802 | A1 * | 1/2010 | Tambourgi et al. | 604/179 |
| 2011/0098609 | A1 * | 4/2011 | Hall et al. | 601/2 |
| 2011/0238021 | A1 * | 9/2011 | Hillhouse | 604/307 |

* cited by examiner

*Primary Examiner* — James H Alstrum Acevedo
*Assistant Examiner* — Daniel L Branson
(74) *Attorney, Agent, or Firm* — Gulf Coast Intellectual Property Group

(57) ABSTRACT

A transdermal analgesic applicator configured to provide a visual signal subsequent sufficient absorption of an analgesic compound ensuing the transdermal analgesic applicator being applied to the skin of a patient. The transdermal analgesic applicator includes a first layer that is impermeable and has integrally formed therewith on at least a portion thereof a plurality of microcapsules containing a thermochromic dye mixture. The first layer having the portion of microcapsules presents a first color at ambient room temperature and a second color at temperature greater than the first temperature as a result of being placed on the skin of a patient. A second layer containing an analgesic compound is secured to the first layer. The first layer changes from the first color to the second color subsequent the first layer changing from the first temperature to the second temperature, which the rate of temperature change is approximately equivalent to the absorption rate of the analgesic compound.

16 Claims, 1 Drawing Sheet

TRANSDERMAL ANESTHETIC APPLICATOR HAVING THERMOCHROMIC INDICATION

FIELD OF THE INVENTION

The present invention relates to a topical and transdermal administration of local anesthetic agents, more specifically but not by way of limitation, a transdermal applicator having a first layer saturated with a general topical anesthetic and a second layer impregnated with at least one thermochromic pigment operable to change colors to indicate that the topical anesthetic has been applied for the correct amount of time.

BACKGROUND

Pain management is critical part of caring for a patient. Local anesthetics are routinely utilized to treat pain either on a daily basis as part of a routine pain management program for ailments such as but not limited to lower back pain, or for temporarily blocking the nerve impulses in an area where an incision or puncturing of the skin needs to be made. The delivery of local anesthetics such as lidocaine through the skin has many advantages. One advantage is that transdermal delivery of medication is very convenient and non-invasive for the patient. Oral application of such drugs must take into account different metabolism and absorption rates subsequent ingestion. Transdermal delivery further has shown to offer a high degree of control over blood concentrations of the delivered drug thus greatly increasing the safety of the delivery.

Routinely in the health management of a patient, injectable medicines must be administered to treat the symptoms or illness of the patient. The medicine is routinely injected in an area of the body where a muscle can be penetrated by the administrator of the injection. Most patients possess fear and anxiety of receiving an injection/puncture. Patients ranging from pediatric to geriatric have fear and/or anxiety regarding the pain associated with receiving an injection/puncture or puncturing of the skin by a needle. This presents challenges for the healthcare worker as they attempt to coerce or distract the patient from the process of administering the injection/puncture. Currently, the normal preparatory process for the injection/puncture site only involves an antiseptic wipe such as but not limited to an alcohol wipe in order to substantially prevent infections. One problem with current administration of an injection or diagnostic procedure requiring the skin of a patient to be punctured is that the process does not involve any application of topical local anesthetics for those patients that may be experiencing significant anxiety about receiving an injection/puncture. The use of topical anesthetics does not occur for several reasons. First, readily available applicators such as transdermal patches are not routinely made available that are suitable to apply the correct dosage of topical anesthetic required to numb an injection/puncture site. Another issue with transdermal applicators of topical anesthetic is that current transdermal applicators offer no method of indication as to whether or not the applicator has been in place for a sufficient amount of time such that the topical anesthetic has been absorbed and the area is now ready for an injection or puncturing of the skin.

Accordingly, there is a need for a transdermal applicator containing a topical anesthetic that is of suitable size to prepare an injection/puncture site on a patient's body and wherein the transdermal applicator provides a visual signal to the healthcare worker subsequent the transdermal applicator having been applied for a sufficient amount of time for the topical anesthetic to have been absorbed into the skin of the patient. Additionally, the transdermal anesthetic applicator should function to substantially decrease the risk of non-compliance for patients that are required to self-administer any injectable medication or puncture their skin as part of a diagnostic procedure by substantially reducing the fear/discomfort associated therewith.

SUMMARY OF THE INVENTION

It is the object of the present invention to provide a transdermal applicator suitable to prepare a portion of a patient's body for an injection/puncture that has a layer saturated with a topical anesthetic.

Another object of the present invention is to provide a transdermal applicator having a topical anesthetic for numbing an injection/puncture site that further includes at least one thermochromic dye impregnated into the outer layer.

Yet another object of the present invention is to provide a transdermal applicator having a topical anesthetic for numbing an injection/puncture site that utilizes a thermochromic dye to provide a visual signal that the transdermal applicator has been in place for a sufficient amount of time.

An additional object of the present invention is to provide a topical anesthetic transdermal applicator that includes an adhesive layer in order to releasably secure the transdermal applicator to an area on the patient's body.

Yet a further object of the present invention is to provide a topical anesthetic transdermal applicator that includes an animated figure that will be aesthetically pleasing for children on the outer layer of the trandermal applicator.

Still another object of the present invention is to provide a topical anesthetic transdermal applicator that functions to reduce a patient's anxiety related to the pain associated with the puncturing of the skin.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
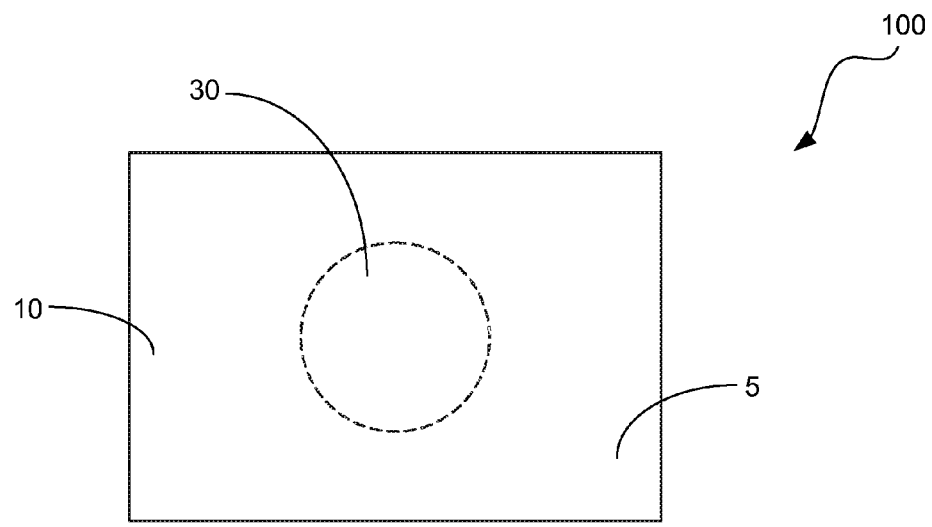
FIG. 1 is a top view of the outer layer of an embodiment of the present invention.

Referring now to the drawings submitted herewith, wherein various elements depicted therein are not necessarily drawn to scale and wherein through the views and figures like elements are referenced with identical reference numerals, there is illustrated a transdermal applicator 100 constructed according to the principles of the present invention.

The transdermal applicator 100 further includes an outer layer 5. The outer layer 5 is manufactured from a suitable durable impermeable material such as but not limited to a thin layer of plastic. The outer layer 5 is substantially solid having no holes for ventilation typically found on outer layers of bandages. While the outer layer 5 is illustrated herein as being generally square in shape, it is contemplated within the scope of the present invention that the outer layer 5 could be formed in numerous different shapes. Although no particular size of the outer layer 5 is required, good results have been achieved utilizing an outer layer 5 that is approximately three inches by three inches.

Figure 2:
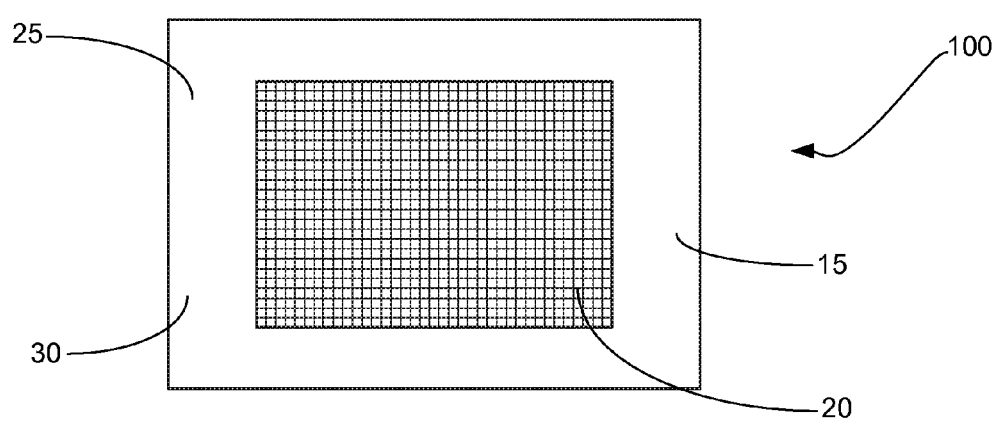
FIG. 2 is a view of the internal layer of an embodiment of the present invention.

Referring in particular to FIG. 2, the interior surface 15 of the outer layer 5 is shown along with the inner layer 20. The interior surface 15 of the outer layer 5 further includes an adhesive layer 25 distributed around the perimeter area 30 of the interior surface 15. It is contemplated within the scope of the present invention that numerous different types of suitable epoxy could be utilized to form the adhesive layer 25 to be distributed around the perimeter area 30 of the interior surface 15 of the outer layer 5. It is further preferred within the scope of the present invention that the adhesive layer 25 be manufactured from an epoxy or other suitable material that has sufficient strength to bond to the user's skin but is released with minimal effort and discomfort to the user. Those skilled in the art will recognize that the adhesive layer 25 could be configured in numerous different manners on the interior surface 15 of the outer layer 5 and still achieve the desired objective of functioning to releasably secure the transdermal applicator 100 to the user's skin in an area to be prepared for an injection/puncture.

Still referring to FIG. 2, the inner layer 20 is secured to the outer layer 5 utilizing suitable durable methods. The inner layer 20 is positioned such that it will be adjacent the user's skin subsequent the transdermal applicator 100 being applied to the user. The inner layer 20 is a conventional gauze absorbent material that functions to retain a topical anesthetic for application. While no particular construction of the inner layer 20 is required, in its preferred embodiment the inner layer 20 consists of nylon fibers embedded into a medical cloth. The inner layer 20 is smaller in area than the outer layer 5. While no particular size of the inner layer 20 is required, good results have been achieved utilizing an inner layer 20 that is approximately two inches by two inches. The inner layer 20 is impregnated therewith a suitable topical analgesic sufficient to provide analgesia to the area of the skin that engages the inner layer 20 subsequent the transdermal applicator 100 being applied to the user in an area where a subsequent injection/puncture is necessary. While no specific type of topical analgesic is required, it is contemplated within the scope of the present invention that the inner layer 20 is impregnated with at least one of the following types of topical analgesics: prilocaine, tetracaine, lidocaine or benzocaine. Additionally, while no specific strength of the aforementioned topical analgesics is required, good results have been achieved utilizing a topical analgesics having a strength within the range of 2.5% to 10% for the concentration of active ingredient to provide timely analgesia to the area of the skin engaged with the inner layer 20.

Referring in particular to FIG. 1, the outer layer 5 further includes an indicating portion 30. The indicating portion 30 functions to provide a visual signal, such as but not limited to a color change, so as to indicate that the transdermal applicator 100 has been secured to the patient for a sufficient amount of time to allow the topical analgesic present on the inner layer 20 to provide the appropriate analgesia. Although the indicating portion 30 is shown in FIG. 1 as being generally circular in shape, it is contemplated within the scope of the present invention that no particular shape of the indicating portion 30 is required. The indicating portion 30 includes microcapsules of thermochromic dyes that are formulated to change color in response being exposed to the temperature of the skin subsequent being placed adjacent thereto. The change in temperature of the outer layer 5 from ambient room temperature to being approximately equivalent to the temperature of the skin of the patient temperature increase typically occurs within three to five minutes. Ambient room temperature is defined herein as being approximately 65 to 72 degrees Fahrenheit, and as is known in the art, the skin of a human being is approximately 82 to 85 degrees Fahrenheit. The time required for the temperature of the outer layer 5 of the transdermal applicator 100 to increase to be approximately equal to the temperature of the skin of the user, is directly correlated to the time required for the topical analgesic impregnated on the inner layer 20 to provide sufficient analgesia to the skin so as to provide a patient significantly reduced discomfort upon receiving an injection/puncture. The concentration of the topical analgesic is calibrated to be present in an amount so as to be absorbed within the time frame in which the outer layer 5 will increase in temperature by at least ten degrees.

The temperature change of the outer layer 5 of the transdermal applicator 100 causes the thermochromic dyes present in the indicating portion 30 to change from an initial color to a second color. This visual signal of color change functions to provide notification that the appropriate amount of time has expired such that the topical analgesic of the inner layer 20 has provided sufficient analgesia to the skin adjacent to and underneath the transdermal applicator 100. As is known in the art, thermochromic dyes are based on mixtures of leuco dyes and other suitable chemicals, displaying a color change in dependence on temperature. The thermochromic dyes integral to the indicating portion 30 are not applied directly thereto. The indicating portion 30 has a plurality of microcapsules of the thermochromic dye material. While no particular size of microcapsule is required, good results have been achieved utilizing a microcapsule that is approximately three to five microns in size. An example of the function of the indicating portion 30 is as follows. The indicating portion 30 having integral thereto a plurality of microcapsules containing a violet lactone, a weak acid and a dissociable salt dissolved in a solvent such as but not limited to dodecanol. The solvent is in its solid state prior to the transdermal applicator 100 being applied to the user's skin at approximately ambient room temperature. In this state the thermochromic dye exists in its lactone leuco form. Subsequent the transdermal applicator 100 being applied to the skin of the user, the outer layer 5 increases in temperature by at least ten degrees. Subsequent exposure to the increased temperature of the skin of the user, the solvent in the microcapsules melts causing the salt to dissociate changing the pH inside the microcapsule. When the pH changes this causes the absorption spectrum of the mixture within the microcapsules to change thus producing the color change of the indicating portion 30. It is contemplated within the scope of the present invention that the indicating portion 30 could change from white or substantially no color to a dark color such as black or red upon being exposed to the temperature change. Those skilled in the art will recognize that numerous different color changes could be accomplished by utilizing different mixtures within the microcapsules of the indicating portion 30.

Figure 3:
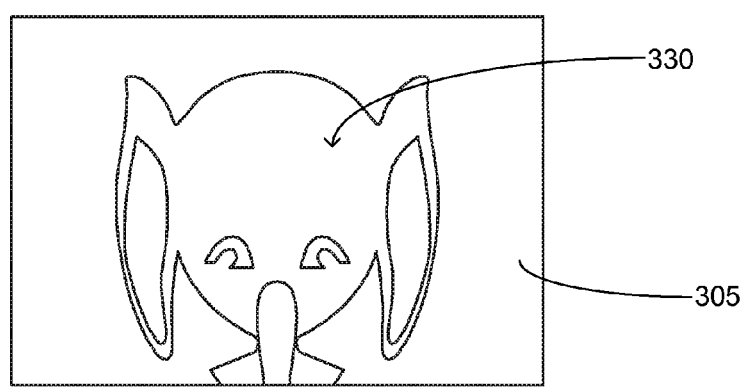
FIG. 3 is a perspective view of an alternative embodiment of an outer layer of the present invention.

Referring in particular to FIG. 3, an alternative embodiment of the outer layer 305 is shown. The outer layer 305 has imprinted thereon a graphical representation 301 of an animal. The outer layer 305 is manufactured identically to the preferred outer layer 5 previously discussed herein. The indicating portion 330 is disposed within the graphical representation 301 imprinted on the outer layer 305. The indicating portion 330 is constructed identically to the indicating portion 30 of the preferred embodiment described herein. The indicating portion 330 functions to display an animal or a portion thereof, in a first color and a second color subsequent exposure to the increase in temperature caused by being placed adjacent the skin of the user. It is further contemplated within the scope of the present invention that the outer layer 305 could further be configured so as to allow a pediatric patient to color a portion thereof utilizing conventional marking devices and not interfere with the indicating portion 330.

A description of the operation of the transdermal applicator 100 is as follows. In use, the user will remove the transdermal applicator 100 from its packaging and place on an area of a patient where an injection/puncture needs to be administered. The adhesive layer 25 present on the perimeter area 30 of the interior surface 15 of the outer layer 5 releasably secures the transdermal applicator 100 to the user. The inner layer 20 is adjacent to the skin and is impregnated with a suitable topical analgesic. Subsequent application of the transdermal applicator 100, the impermeable outer layer 5 increases in temperature by at least ten degrees Fahrenheit. The temperature change causes the indicating portion 30 to change from a first color to a second color. The time required for the color change of the indicating portion 30 to take place is calibrated to be approximately the same time required for the topical analgesic to provide the appropriate analgesia to the skin. The transdermal applicator 100 is then removed subsequent the indicating portion 30 changing from a first color to a second color and the area is now prepared so an individual can insert a needle into the area with substantially reduced discomfort.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A transdermal analgesic applicator comprising:
    a first layer, said first layer configured in a substantially planar manner, said first layer generally square in shape, said first layer being manufactured of an impermeable material;
    a second layer, said second layer adjacent said first layer, said second layer being secured to said first layer, said second layer being impregnated with an analgesic compound;
    an indicator, said indicator integrally formed with said first layer, said indicator operable to provide a visual signal of an increase in the temperature of said first layer; and
    wherein said indicator has a first color within a first temperature range of 65 to 72 degrees Farenheit and a second color within a second temperature range of 82 to 85 degrees Farenheit.

2. The transdermal analgesic applicator as recited in claim 1, wherein said indicator further includes microcapsules containing therein a thermochromic dye mixture.

3. The transdermal analgesic applicator as recited in claim 2, wherein the analgesic compound impregnated within said second layer is absorbed transdermally through a patient's skin in a time period that is approximately equivalent for the time period required for said indicator to transition from said first color to said second color.

4. The transdermal analgesic applicator as recited in claim 3, wherein said second layer is impregnated with at least one of the following analgesic compounds: prilocaine, tetracaine, lidocaine or benzocaine.

5. A transdermal analgesic applicator for applying an analgesic compound to an area of a patient's skin comprising:
    a first layer, said first layer being generally square in shape and configured in a substantially planar manner, said first layer having a first surface and a second surface, said first layer manufactured of an impermeable material;
    a second layer, said second layer integrally secured to said second surface of said first layer, said second layer configured to be superposed an area of the skin of a patient, said second layer being impregnated with an analgesic compound;
    an indicating portion, said indicating portion integral to said first surface of said first layer, said indicating portion having a first color and a second color, said indicating portion operable to present said first color at a first temperature and said second color at a second temperature; and
    wherein said first temperature is within the range of 65 to 72 degrees Farenheit and said second temperature is within the range of 82 to 85 degrees Farenheit.

6. The transdermal analgesic applicator as recited in claim 5, wherein said indicating portion presents said first color at said first temperature wherein said first color is a lighter color than said second color.

7. The transdermal analgesic applicator as recited in claim 6, wherein the analgesic compound has an active ingredient range between 2.5 and 10%.

8. The transdermal analgesic applicator as recited in claim 7, wherein said indicating portion further includes microcapsules, said microcapsules containing therein a thermochromic dye, said thermochromic dye operable to control the color of said indicating portion.

9. The transdermal analgesic applicator as recited in claim 8, wherein the analgesic compound impregnated within said second layer has a transdermal absorption rate approximately equivalent to the time required for said indicating portion to transition from said first temperature to said second temperature subsequent the transdermal analgesic applicator being applied to the skin of a patient.

10. The transdermal analgesic applicator as recited in claim 9, wherein said indicating portion is annular in shape.

11. The transdermal analgesic applicator as recited in claim 10, wherein said second layer is impregnated with at least one of the following analgesic compounds: prilocaine, tetracaine, lidocaine or benzocaine.

12. A transdermal analgesic applicator configured to apply an analgesic compound to an area of a patient's skin to provide sufficient analgesia for a subsequent insertion of a needle, wherein the patient's recognition of the needle insertion is substantially reduced comprising:
    a first layer, said first layer being square in shape and configured in a substantially planar manner, said first layer having a first surface and a second surface, said first layer manufactured of an impermeable material, said first layer having an adhesive material disposed on the perimeter of said second surface, said first layer being approximately three inches by three inches;

a second layer, said second layer integrally secured to said second surface of said first layer, said second layer being approximately two inches by two inches, said second layer manufactured from medical cloth embedded with nylon fiber, said second layer configured to be superposed an area of the skin of a patient, said second layer being impregnated with an analgesic compound;

an indicating portion, said indicating portion integral to said first surface of said first layer, said indicating portion having a first color within a first temperature range and a second color within a second temperature range, said indicating portion being a graphical representation of an animal, said indicating portion operable to present said first color within said first temperature range and said second color at a within said second temperture range;

a plurality of microcapsules, said plurality of microcapsules being formulated to respond to temperature change, said plurality of microcapsules containing therein a thermochromic dye, said thermochromic dye operable to control the color of said indicating portion; and wherein said first temperature range is within 65 to 72 degrees Farenheit and said second temperature range is within 82 to 85 degrees Farenheit.

13. The transdermal analgesic applicator as recited in claim 12, wherein the analgesic compound has an active ingredient range between 2.5 and 10%.

14. The transdermal analgesic applicator as recited in claim 13, wherein said second color is a darker color than said first color.

15. The transdermal analgesic applicator as recited in claim 14, wherein the analgesic compound impregnated within said second layer has a transdermal absorption rate approximately equivalent to the time required for said indicating portion to transition from said first temperature range to said second temperature range subsequent the transdermal analgesic applicator being applied to the skin of a patient.

16. The transdermal analgesic applicator as recited in claim 15, wherein said second layer is impregnated with at least one of the following analgesic compounds: prilocaine, tetracaine, lidocaine or benzocaine.

* * * * *